(12) United States Patent
Dierks (10) Patent No.: US 7,524,326 B2
(45) Date of Patent: Apr. 28, 2009

(54) BONE SCREW

(75) Inventor: Michael Dierks, Wermelskirchen (DE)

(73) Assignee: Signus Medizintechnik GmbH, Alzenau (DE)

( * ) Notice: Subject to any disclaimer, the term of this patent is extended or adjusted under 35 U.S.C. 154(b) by 0 days.

(21) Appl. No.: 10/938,045

(22) Filed: Sep. 10, 2004

(65) Prior Publication Data

US 2005/0059973 A1  Mar. 17, 2005

(30) Foreign Application Priority Data

Sep. 12, 2003  (DE)  ............................... 203 14 297

(51) Int. Cl.
*A61B 17/86* (2006.01)
(52) U.S. Cl. .................................................. 606/308
(58) Field of Classification Search ................. 606/61, 606/72, 73, 246, 264–274, 300, 301, 305–308
See application file for complete search history.

(56) References Cited

U.S. PATENT DOCUMENTS

| 5,505,731 | A | * | 4/1996 | Tornier ........................ 606/61 |
| 5,569,247 | A | | 10/1996 | Morrison | |
| 5,662,651 | A | * | 9/1997 | Tornier et al. ................. 606/60 |
| 5,716,357 | A | | 2/1998 | Rogozinski | |
| 6,004,322 | A | | 12/1999 | Bernstein | |
| 6,423,064 | B1 | | 7/2002 | Kluger | |
| 6,478,798 | B1 | * | 11/2002 | Howland ..................... 606/61 |
| 6,565,569 | B1 | * | 5/2003 | Assaker et al. ................ 606/61 |

FOREIGN PATENT DOCUMENTS

| DE | 199 21 551 | 5/1999 |
| DE | 199 44 120 | 9/1999 |
| DE | 199 50 075 | 10/1999 |

* cited by examiner

*Primary Examiner*—Eduardo C Robert
*Assistant Examiner*—Richard Shaffer
(74) *Attorney, Agent, or Firm*—Fildes & Outland, P.C.

(57) ABSTRACT

A bone screw is disclosed for attaching a spinal fixing element. The bone screw includes a threaded screw shank that can be fixed in place in a bone and a screw head having a fastening area for fastening a fastening device for the spinal fixing element. The fastening area includes a threaded section for fixing the fastening device in place. The screw head includes a recess differing from a threaded section. The recess has a longitudinal axis and allows for non-sliding accommodation of an extension of the fastening device laterally to the longitudinal axis of the recess. The extension of the fastening device engages the recess, the fastening device is rotatable about the longitudinal axis of the recess, and the threaded section extends in the longitudinal direction of the recess. The threaded section may be a hole and, together with the recess, a stepped hole.

17 Claims, 5 Drawing Sheets

SECTION A-A

Fig. 1f

SECTION A-A

Fig. 2e

SECTION A-A

SECTION A-A

SECTION B-B

Fig. 3d

BONE SCREW

TECHNICAL FIELD

The invention relates to a bone screw for attaching a spinal fixing element, especially as a pedicle screw, with a screw shank that can be fixed in place in a bone, especially a vertebra, with a thread for screwing into the bone, and with a screw head with a fastening area for a fastening device, by means of which the spinal fixing element can be fixed in place, where the fastening area displays a threaded section for fixing the fastening device in place, and where a fastening device for fixing a spinal fixing element in place on the bone screw can also be encompassed.

BACKGROUND OF THE INVENTION

Various bone screws of this kind are known and can, for example, be used to stabilize bones, or fix them in place relative to each other, especially to stabilize and fix the spinal column, in that the respective bone screws are screwed into the bones to be fixed, such as vertebral bodies, and fastened by means of the fixing device, such as a rod-like longitudinal support for osteosynthesis, which is fixed in place on the associated fastening device.

A bone screw of this kind with fastening device is known from DE 199 44 120 A1. The fastening area of the bone screw for the fastening device is designed in the shape of a truncated cone formed on a partially spherical screw head, where the truncated cone, which expands preferably conically towards the screw shank, displays a threaded hole to accommodate a threaded screw, by means of which the fastening device, designed as a clamp, can be fixed in place on the screw head. This is intended to make it possible, even after positioning of the bone screw, for the location of the longitudinal support to be varied freely relative to its longitudinal axis.

However, it has proved to be disadvantageous with a bone screw of this kind that, when the bone screw is implanted, secure arrangement and simple handling of the clamps on the truncated cone during fixing in place and/or alignment of the spinal fixing element is not always possible in the desired way because of the projecting truncated cones. For example, with this arrangement, the clamp with the arch serving to accommodate the fixing rod is located very close to the spinous process of the vertebral body. Moreover, owing to the relatively low height of the truncated cone, there is a risk, in the event of pre-mounting of the clamps, of them slipping off the truncated cone. Furthermore, it is often necessary to deform the fixing rod to adjust it to the target position of the vertebral bodies. However, insertion of the connecting rod into the corresponding receptacles of the clamps is sometimes quite inconvenient with the known bone screw because of the given arrangement of the clamps. On the other hand, attachment of the connecting rod with pre-mounted clamps is difficult, especially in the event of long instrumentation extending over several vertebral bodies, because the clamps have to be levered over the truncated cones of the implanted bone screws.

In addition, DE 199 21 551 and EP 641 548 disclose bone screws with superficial toothing for fixing the fastening device in various angular positions. In this context, the toothing is usually provided over a large area on a convex section of the spherical head or on a plane of section of the sphere. However, the application of toothing of this kind is relatively complex and expensive.

SUMMARY OF THE INVENTION

The object of the invention is to develop a generic bone screw in such a way that the spinal fixing element can be fixed in place on the bone screw relatively easily and securely, also giving consideration to pre-mounting of the fastening device on the bone screw, which can also be implanted by minimal invasive surgery where appropriate.

According to the invention, the object is solved by a bone screw according to the present invention. In particular, the screw head can display a recess differing from a threaded section, with a longitudinal axis, designed for non-sliding accommodation of a retaining area of the fastening device laterally to the longitudinal axis of the recess, where the recess is designed in such a way that it can accommodate, in laterally non-sliding fashion, a retaining area of the fastening device that engages the recess and is of essentially congruent design, and in such a way that the threaded section extends at least essentially in the longitudinal direction of the recess.

An extension of the fastening device can thus be inserted into the recess, this preventing the fastening device from unintentionally slipping off the screw head, even during difficult manipulations of a spinal fixing element, such as bending thereof. In this context, the recess can extend relatively far into the screw head, meaning that a relatively large contact surface for the fastening device can be provided on the inside of the screw head, as a result of which a stable assembly is obtained, also in pre-mounted condition, and high retention forces can be absorbed when the fastening device is fixed in place. Furthermore, the design according to the invention makes it possible for the outer contour of the screw, and also the cross-sectional design of the recess and/or the engaging retaining area, to be optimally adapted to the respective requirements, independently of other necessities, e.g. for the screw head to be very largely designed as a spherical head. Moreover, the bone screw with fastening device can be implanted by minimal invasive surgery.

The invention additionally provides a fastening device for interacting with a bone screw of this kind, where the fastening area displays an extension that can engage the recess in the bone screw. Further advantageous embodiments of the bone screw, and of the fastening device, result from the following and the sub-claims.

Preferably, the recess can accommodate the retaining area of the fastening device over its whole circumference in laterally non-sliding fashion. The recess is preferably closed over its whole circumference, without being limited to this. Furthermore, in pre-mounted condition, the fastening device is preferably capable of infinitely variable rotation over its whole circumference relative to the screw shank.

Preferably, the recess in the screw head for accommodating the retaining area of the fastening device is of essentially cylindrical design, this also encompassing a conical design, where the threaded section is arranged essentially concentrically to the recess.

Advantageously, referred to the direction of insertion of the connecting means for fixing the fastening device in place, the recess precedes the threaded section and displays a greater diameter than the latter. As a result, the recess can display a relatively large diameter, and the recess and the threaded section are easy to make in the screw head in terms of production engineering, especially if the latter is designed as a threaded hole. Furthermore, to fix the fastening device in place, the associated connecting means can first simply be positioned in the recess, thereby achieving a certain degree of pre-assembly, the connecting means only subsequently being screwed tight on the threaded section.

Advantageously, the recess and the threaded section designed as a threaded hole are designed in the manner of a stepped hole and separated from each other merely by a shoulder. Preferably, the shoulder displays a top side that runs perpendicular to the longitudinal axis of the recess and is immediately followed by the threaded hole. Where appropriate, however, the threaded section and the recess can also be separated from each other by a transitional area extending in the longitudinal direction of the recess.

Advantageously, the longitudinal axis of the threaded section, and thus also the preferably concentric longitudinal axis of the recess, is inclined relative to the longitudinal axis of the screw shank, this resulting in simple handling of the bone screw. The angle enclosed between the longitudinal axes of the threaded section and the screw shank is preferably up to 0°, e.g. approximately 30° to 60° or approximately 45°, without being limited to this. Where appropriate, the longitudinal axis of the threaded section can also be perpendicular to the longitudinal axis of the screw shank, or also coaxial with it.

Advantageously, the recess tapers towards the inside of the screw head, as a result of which the retaining area of the fastening device inserted into the recess can center itself, jamming in the recess being prevented at the same time. The taper can be conical, and the longitudinal section of the recess wall can also be of curved design, where the taper can become increasingly narrow with increasing distance from the insertion opening of the recess.

It has proved to be advantageous if the recess tapers conically with an angle of 1° to 20° between the wall of the recess and the longitudinal axis of the recess, preferably approximately 2° to approximately 10° to 15°, e.g. approximately 7.5°, without being limited to this.

The shoulder radially surrounding the recess and the threaded section on the outside can have roughly the same radial extension as the shoulder radially surrounding the recess on the outside. It has proved to be particularly advantageous if the shoulder radially surrounding the threaded section on the outside has a larger radial extension than the shoulder radially surrounding the recess on the outside, as a result of which the recess has a relatively large diameter in the region of the insertion opening for the retaining area of the fastening device.

Preferably, the screw head is convex, in the manner of a spherical surface, over the height of at least a partial area of the recess, or over the entire height of the recess. As a result, the screw head can be designed with a relatively great material thickness in the area of the recess, while the recess can simultaneously have a relatively large diameter, this ensuring very stable fastening of the spinal fixing element and, at the same time, a screw head geometry favorable for insertion and handling of the implant.

The recess can display a circular or non-circular, particularly polygonal cross-section, where contact areas for the extension of the fastening device engaging the recess can lie on an arc of a circle. The polygonal cross-section can, in particular, be of a design with three to twelve or more sides, preferably five to eight sides. Preferably, the cross-sections of the contact areas of the recess, and of the retaining area of the fastening device that engages it, which comes into contact with the wall of the recess, are matched in such a way that one of the cross-sections is of circular design and the other cross-section of non-circular design with at least three contact areas distributed around the circumference, particularly of polygonal design. For example, the cross-section of the recess or the cross-section of the retaining area of the fastening device can be of circular design, where the cross-section of the respective corresponding component is of non-circular, particularly polygonal, design. The polygons can, in particular, be regular polygons. This enables easier rotation of the fastening device about the longitudinal axis of the recess when the fastening device is pre-mounted on the bone screw, without the entire lateral surfaces of the recess wall or the retaining area of the fastening device coming into contact with each other, as well as preventing jamming of the fastening device when high clamping forces are exerted. It goes without saying that more or less pronounced deviations from a polygonal design are possible, e.g. in the form of rounded transitional areas at the corners and/or rounded intermediate areas between the contact areas. The contact areas can thus be of linear or plane design.

Preferably, the height of the inner wall of the recess extends, on the side of the recess most closely adjacent to the screw shank, beyond the extension of the lateral surface of the screw shank, into the screw head. In this context, the side of the recess most closely adjacent to the screw shank is defined by a plane spanned by the longitudinal axis of the recess and the longitudinal axis of the screw shank and determined by the direction of inclination of the longitudinal axis of the recess. The lateral surface of the screw shank can be defined by the envelope of the threaded section, or the envelope of the shank area determined by the respective base of the threaded sections. As a result, the recess can display a great depth, without influencing the geometry of the screw head surface, which can be designed appropriately, independently of the design of the recess or its depth.

Preferably, the recess extends into the screw head in such a way that the cross-section limiting the depth of the recess, or the bottom of the recess, is located roughly at the level of, or on, the side of the intersection of the longitudinal axis of the screw shank and the longitudinal axis of the recess facing away from the opening of the recess. In this context, the bottom of the recess can be defined by the lower circumferential edge of the recess, and the bottom of the recess can, of course, display an opening that can be followed by a threaded hole, for example. Given an essentially spherical design of the screw head, the above-defined intersection corresponds to the mid-point of the sphere. This great depth of the recess permits very secure and stable pre-mounting of the fastening device, and even in the event of high retention forces, only a relatively low surface pressure of the mutually contacting contact areas of the retaining area of the fastening device and the inner wall of the recess is achieved.

Preferably, the screw head is essentially designed as a spherical head or a partially spherical head, where the spherical head is preferably of spherical design with the exception of lateral, opposite flat areas and other retaining areas for fastening devices of importance for the respective implant, such as extension rods or the like. The spherical-head design preferably also extends over part of the height, or the entire height, of the recess.

Preferably, the recess, which can be followed by a threaded section in the form of a threaded hole, is designed as a through-hole passing through the screw head.

The fastening device according to the invention, which serves to fix a spinal fixing element in place on a bone screw, particularly a bone screw described above, displays an essentially cylindrical extension for insertion into a recess of a corresponding bone screw, where the extension displays a through-hole for a connecting element for fixing the fastening device in place on the screw head. A connecting element of this kind can, in particular, be designed as a stud. The essentially cylindrical shape of the extension is also taken to encompass a polygonal shape or other non-circular shape described further below, where the extension displays contact surfaces that can be positioned against an inner wall of a recess and lie on an arc of a circle. Furthermore, the essentially cylindrical design is also taken to encompass a conical or other rotationally symmetrical shape of the extension or of an envelope thereof.

Preferably, the fastening device displays a leg facing towards the screw shank and a leg facing away from it, between which a spinal fixing element can be fixed in place. Other designs of the fastening device are, however, also possible. The legs can be integrally molded on each other in one piece, for instance in the manner of a clamp, although the legs can also be detachably fastenable to each other. Preferably, the extension of the retaining area of the fastening device, which can be positioned in the recess, is located on the leg facing towards the screw shank. Where appropriate, however, the extension can also be located on the leg facing away from the screw shank, which reaches through the adjacent leg in order to engage the recess. In this context, the fastening device is preferably fastened on the screw head by the same fastening means as also used for fixing the spinal fixing element in place, although two independent fastening means, such as studs, can also be provided where appropriate.

Preferably, the retaining area of the fastening device contacts the spherical-head screw only in the area of the lateral surface of the extension; where appropriate, an additional contact surface for the fastening device can also be formed by the circumferential edge of the screw head surrounding the recess on the outside, which can constitute a surface area of the screw head, and/or by the area of the recess opposite the free end of the extension, such as a shoulder provided between the threadless recess and the threaded section. Where appropriate, the leg of the fastening device facing towards the screw head can also contact the surface of the screw head, for instance at a connecting area of the leg with the extension, or over a more extensive area of the circumference, for example also over the entire circumference.

The extension can display a circular or polygonal outer cross-section, where, in the latter case, the recess preferably displays a circular cross-section. The extension and the recess can generally be designed in such a way that the extension only contacts the inner wall of the recess over part of its lateral surface located in the recess. In this context, the extension can be designed with three to twelve or more sides, preferably five to eight sides. Preferably, the polygon is equilateral in each case, and this can also apply to a polygonal design of the recess. It goes without saying that, also in the event of a polygonal design of the extension or the recess, this design can deviate to a greater or lesser extent from the ideal form, and that rounded areas can be provided at the transitional areas between different surfaces, or the surfaces themselves can display a slight curvature, preferably a concave curvature.

The contact areas of the recess or the extension can be designed as strip-like areas, extending in the longitudinal direction of the extension or the longitudinal direction of the recess, which can be brought into linear or plane contact with the corresponding contact area of the respective corresponding component. The strip-like areas can, in particular, be located in the transitional areas of outer surfaces of the extension that deviate more strongly from a circular cross-section, e.g. in the transitional area of plane lateral surfaces of the extension or the recess. The strip-like areas are preferably distributed evenly over the circumference of the extension or the recess. The strip-like areas can extend around the circumference of the extension or the recess by less than 10°, preferably less than 5°, or by approximately 2° or less. The strip-like areas can themselves display an essentially circular outer contour, or be in the form of essentially plane bevels of areas of the lateral surface of the extension or the recess, meaning that two linear contact areas a slight distance apart are essentially provided that extend in the longitudinal direction of the recess or the extension.

The leg of the fastening device facing away from the extension can display a through-hole for passing through a fastening means for fixing the fastening device in place on a corresponding bone screw.

Preferably, the mid-point of a retaining area for fixing in place the spinal fixing element, such as a longitudinal rod of a fixing device, is located roughly at the level of the outside opening aperture of the recess, or above the same, such as at the level of, or above, the piercing point of the longitudinal axis of the recess through the spherical envelope of the screw head surface. The height of the retaining area mid-point in the longitudinal direction of the recess can be located $\geq 1.1$ to 1.2 times, or >1.5 times or 1.75 times, the spherical-head radius from the mid-point of the spherical head or the intersection of the longitudinal axis of the screw shank and the longitudinal axis of the recess.

The lower leg of the fastening device can rest on the surface of a segment of the sphere of the screw head, or be located above it.

Preferably, the bone screw with the associated fastening device fixed in place on it in the normal manner is designed in such a way that, in all possible target positions of the fastening device, the bone screw can be screwed into a bone, especially a vertebra, up to the screw head. This applies, in particular, to a target position in which the retaining area of the fastening device for a spinal fixing element displays the shortest possible distance from the end of the screw shank facing away from the screw head or is located in the position facing the screw shank in the plane spanned by the longitudinal axis of the recess and the longitudinal axis of the screw shank.

When not fixed in place, the extension can be rotatable about the longitudinal axis of the recess relative to the screw head, at least about part of the circumference, such as 90° or more, or 180° or more, or the full circumference, particularly being freely rotatable.

Preferably, a bone screw with associated fastening device is provided with a guide, by means of which a connecting means, such as a stud for fixing the fastening device in place on the screw head, can be accurately guided through the fastening device to the associated threaded section of the screw head. This facilitates location and fixing in place of the connecting means on the screw head. This guide can be provided by the leg facing towards and/or away from the screw head, by the extension of the fastening device and/or by another suitable area of the bone screw and/or the fastening device. In particular, a through-hole in the extension can be provided that is designed to be concentric to the threaded section designed as a threaded hole and, taking the thread into account, displays roughly the same inside diameter as the threaded hole.

These and other features and advantages of the invention will be more fully understood from the following detailed description of the invention taken together with the accompanying drawings.

BRIEF DESCRIPTION OF THE DRAWINGS

FIG. 1 An illustration of a bone screw according to the invention, in a rear view (FIG. 1a), a side view (FIG. 1b), a front view (FIG. 1c), a cross-section A-A pursuant to FIG. 1b (FIG. 1d, f), and a perspective view (FIG. 1e), FIG. 2 A fastening device for a bone screw pursuant to FIG. 1, in a perspective view (FIG. 2a), a top view (FIG. 2b), a side view (FIG. 2c), a bottom view (FIG. 2d), along section A-A pursuant to FIG. 2b (FIG. 2e), and in an alternative embodiment (FIG. 2f).

DETAILED DESCRIPTION OF THE INVENTION

Bone screw 1 pursuant to FIG. 1 is used for attaching a spinal fixing element, such as a longitudinal rod, and can particularly be used as a pedicle screw. The bone screw can be screwed into a vertebra or another bone by screw shank 3 provided with thread 2. Screw head 4 is essentially designed as a spherical head, which displays lateral flat areas 5, these being provided with retaining areas for a connecting rod (not shown) in the form of grooves 7, running parallel to the longitudinal axis of the shank, which corresponding extensions of the connecting rod can engage in the familiar manner. Furthermore, provided on the rear side of the screw head facing away from recess 8 is a retaining area in the form of groove 9, extending transverse to the longitudinal axis of the shaft, which serves for coupling an alternatively designed connecting rod or another device for use with the bone screw according to the invention.

The essentially or exactly cylindrical and preferably threadless recess 8 serves to accommodate a fastening area of fastening device 30 shown in FIG. 2, designed as extension 34, where the fastening device is freely rotatable about the longitudinal axis of the recess when not fixed in place. In this context, the essentially cylindrical extension is retained in the recess without lateral play and in non-skewing fashion. Non-rotating fixing in place of fastening device 30 on bone screw 1 is accomplished by a threaded section designed as threaded hole 10, which can accommodate a corresponding fastener such as stud 41 or similar, by means of which the associated component of the spinal fixing element can simultaneously be fixed in place on the bone screw. In this context, the stud 41 displays, between the screw head and the thread, a circumferential groove 42, at least areas of which are located at the level of the gap between the two legs of the fastening device; according to the practical example, the base of the groove is at the level of the top side of the leg facing towards the screw head. In this context, threaded hole 10 is located concentrically to cylindrical recess 8. In the context, the preferably threadless recess 8 faces towards the top side of the screw head, and the threaded section is located downstream in the direction of insertion of the stud 41 or on the side facing away from insertion opening 11 of the recess. Over its entire depth, recess 8 displays a larger diameter than threaded hole 10. Recess 8 and threaded hole 10 are designed in the manner of a stepped hole, each being surrounded on the outside by an edge 12 or shoulder 13 at the end facing towards insertion opening 11. In this context, edge 12 lies in a plane of a segment of a sphere that cuts off the spherical screw head. Shoulder 13, radially surrounding the threaded section on the outside, displays a larger radial extension than the shoulder or edge 12 radially surrounding the recess on the outside.

According to the practical example, recess 8 is of conical design, tapering towards the mid-point of the screw head. The inclination of the inner wall of the recess and the inclination of the corresponding contact surfaces of the extension match, the inclination relative to the longitudinal axis of the recess being approximately 7°. The angle between longitudinal axis 14 of recess 8, or the concentrically arranged threaded section, and longitudinal axis 6 of the screw shank is approximately 45°.

Figure 2A:
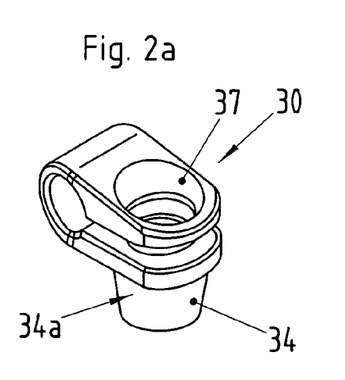
Figure 2B:
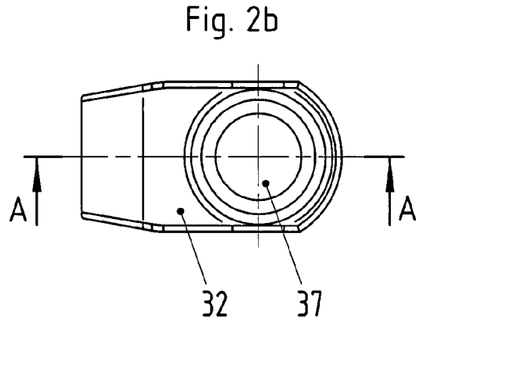
Figure 2C:
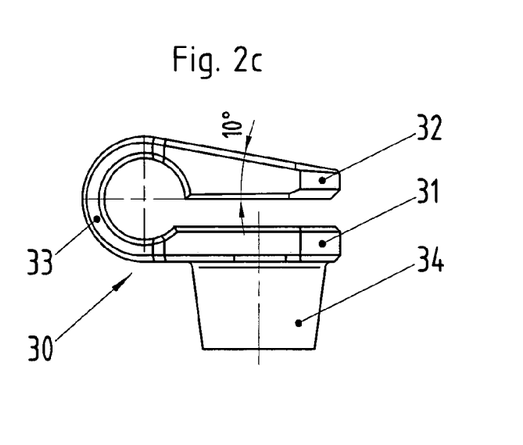
Figure 2D:
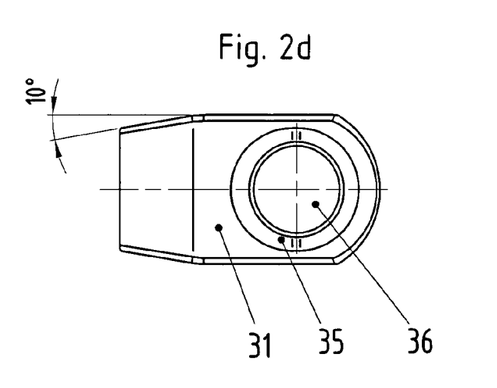
Figure 2E:
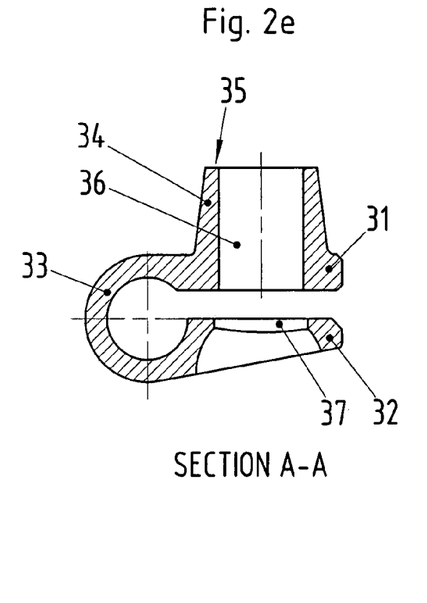
Figure 2F:
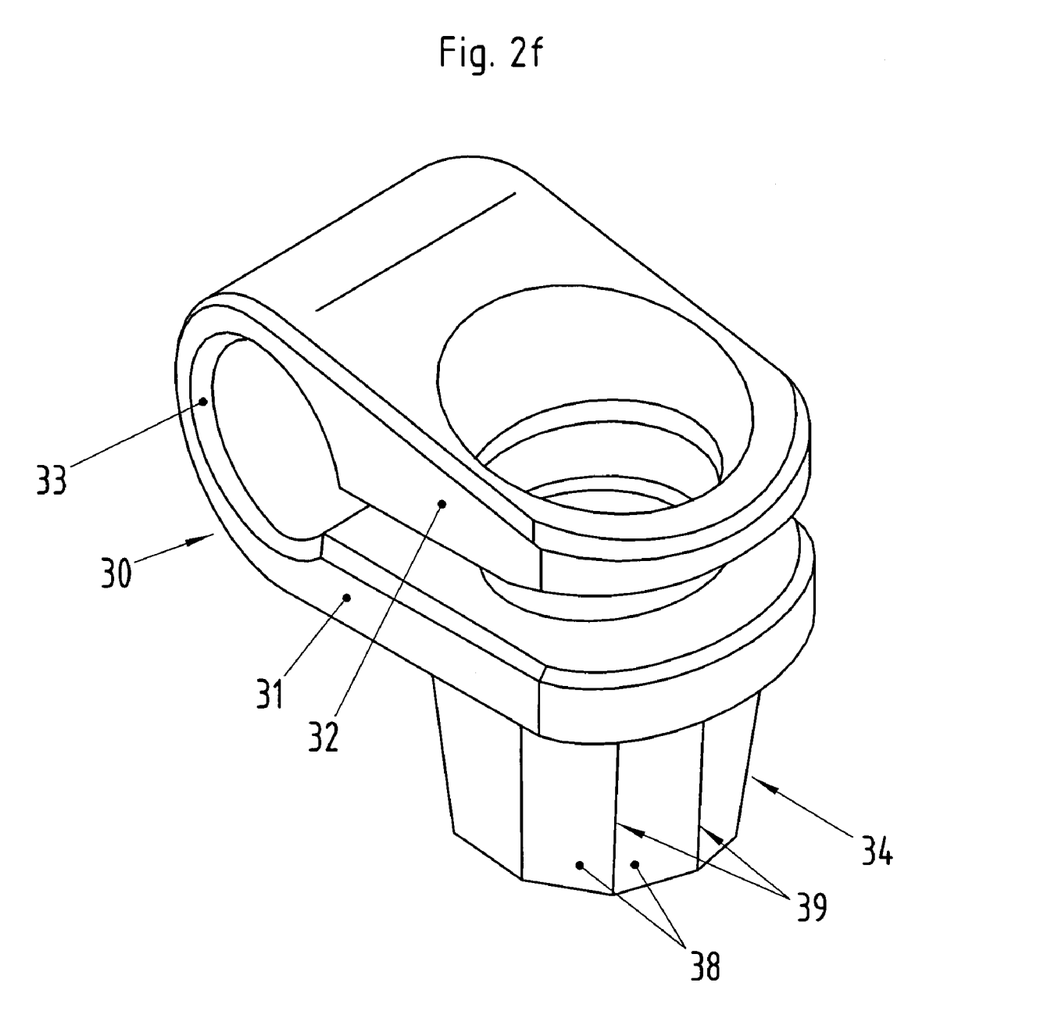

Pursuant to the practical example, the recess displays a circular cross-section, and lateral surface 34a of extension 34, which comes into contact with inner wall 15 of the recess, is, according to FIG. 2a, of rotationally symmetrical or conical design with the same cone angle, such that the surfaces of the extension and the recess wall can be brought into contact with each other over the full circumference. Pursuant to the further embodiment according to FIG. 2e, essentially cylindrical extension 34 displays a polygonal cross-section, tapering towards the free end. This creates strip-like contact areas 39, which are each located between receding, preferably plane areas 38 and extend in the longitudinal direction of the extension or, when the fastening device is mounted, essentially in the longitudinal direction of the recess. Strip-like contact areas 39 can make linear or plane contact with a circumferential area on inner wall 15 of the recess. The circumferential angular extension of each of strip-like contact areas 39 can, for example, be approximately 5°, without being limited to this. The strip-like contact areas can avoiding jamming of the components against each other when high forces are applied. In this context, strip-like contact areas 39 extend over the entire height of extension 34, although this is not absolutely necessary.

Figure 1A:
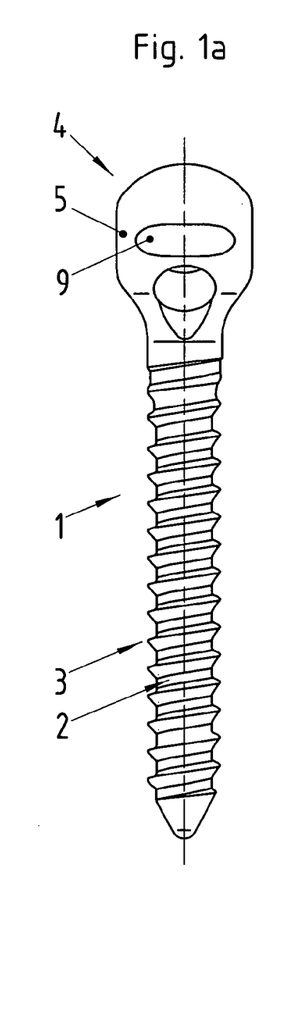
Figures 1B, 1C, 1D:
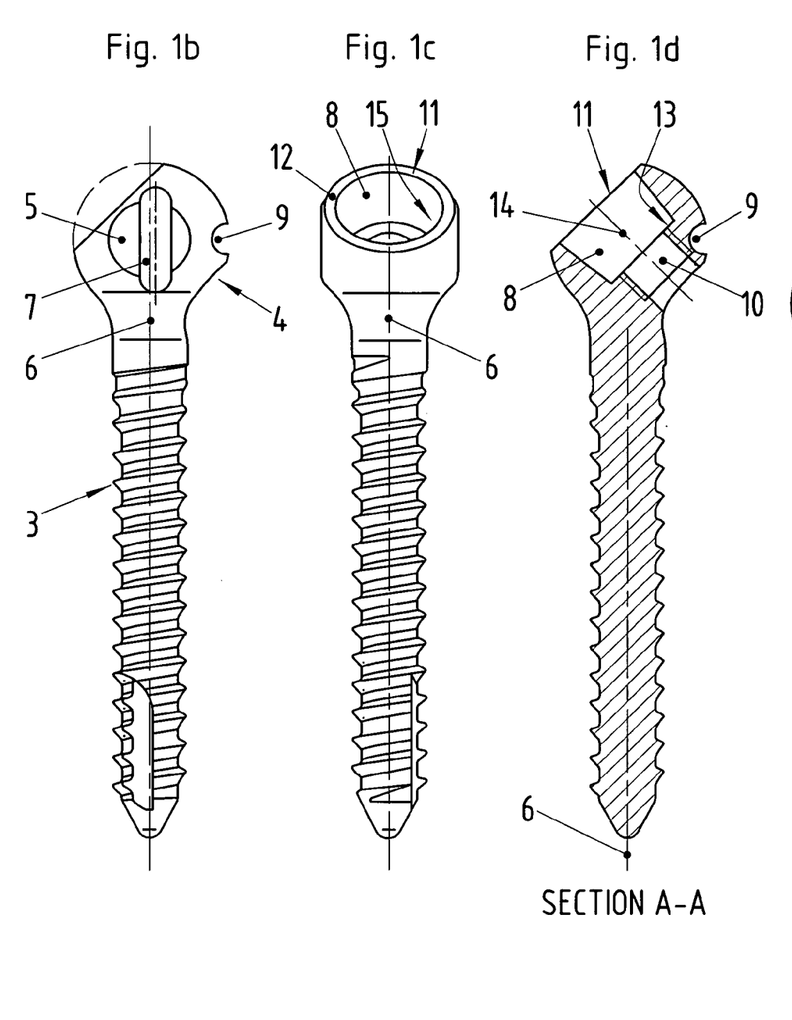
Figure 1E:
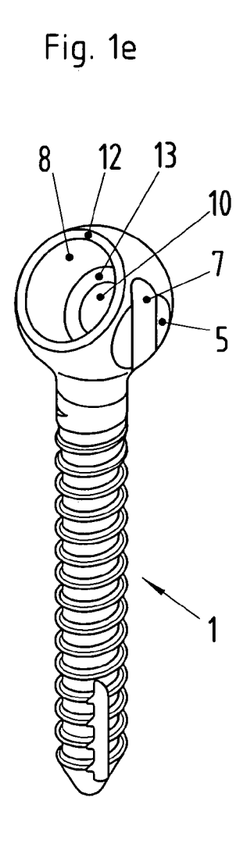
Figure 1F:
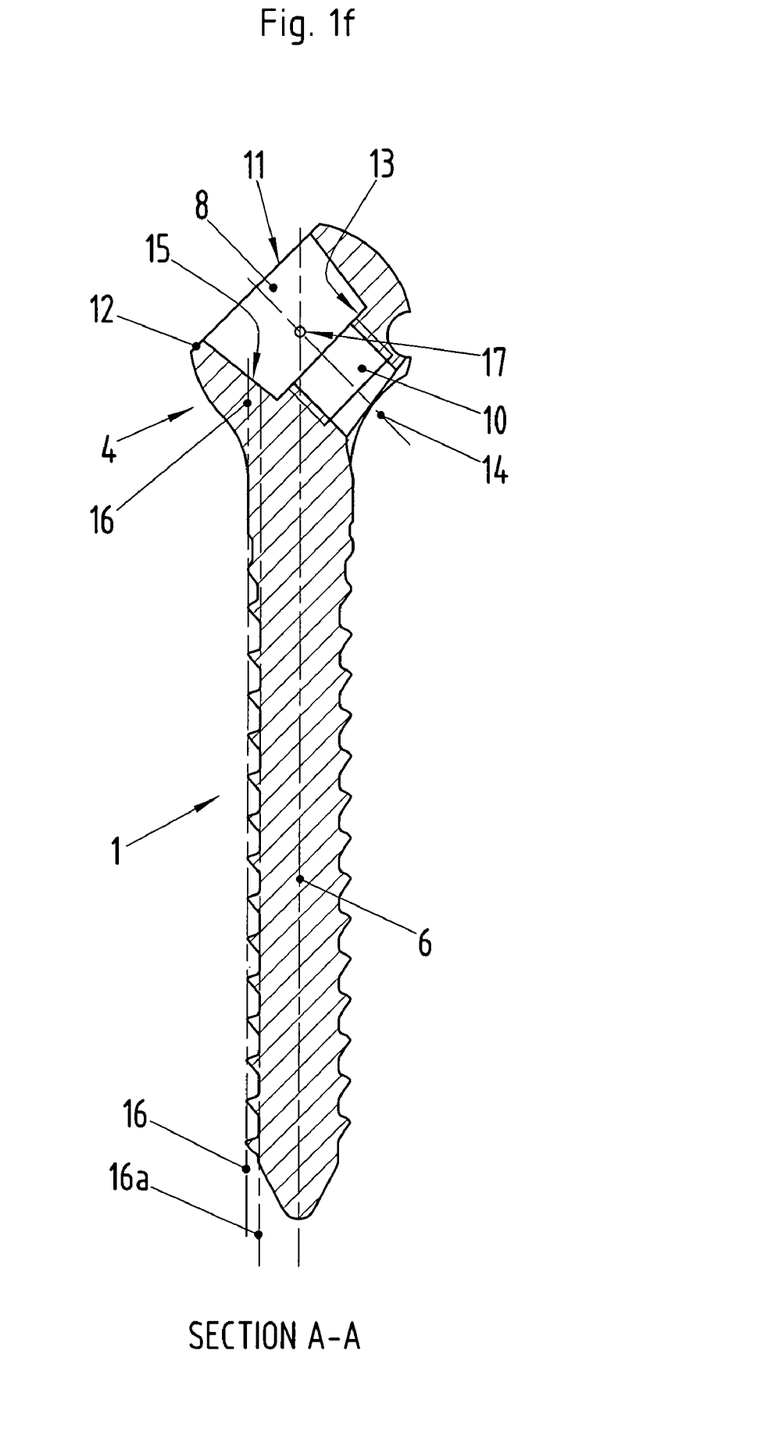

Pursuant to FIG. 1f, on the side of recess 8 most closely adjacent to the screw shank, which lies in the plane spanned by longitudinal axis 14 of the recess and longitudinal axis 6 of the screw shank, the height of inner wall 15 of the recess extends beyond the extension of lateral surface 16 of the screw shank, into the screw head. In this context, the lateral surface is the envelope of the screw shank, including thread, although this can, where appropriate, this can also refer to the envelope of the screw shank referred to the base of the respective thread flights (envelope 16a). As a result, the recess can extend very far into the screw head, independently of the design of the outer surface of the latter.

Referred to the longitudinal axis of the recess, the cross-sectional area limiting the depth of the threadless recess, which is formed here by shoulder 13 or the bottom of the recess, is located on the side of the intersection of the longitudinal axis of the screw shank and the longitudinal axis of the recess facing away from the opening of the recess, or also at the level of the intersection. This can also apply accordingly to the free end of the extension located in the recess when the fastening device is fixed in place, although it can also be a distance away from the bottom of the recess. The end of the threadless recess is thus located on the side of the geometrical mid-point 17 of the screw head facing away from insertion opening 11 of the recess. According to the practical example, recess 8 and threaded hole 10 are designed as a stepped hole with through-hole 18, this resulting in advantages in terms of production engineering.

Figure 3A:
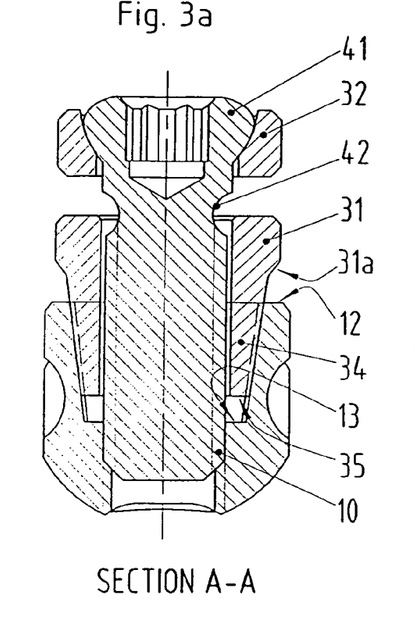
FIG. 3 Various views of a bone screw pursuant to FIG. 1 (partly only selected areas) and a fastening device pursuant to FIG. 2.
Figure 3B:
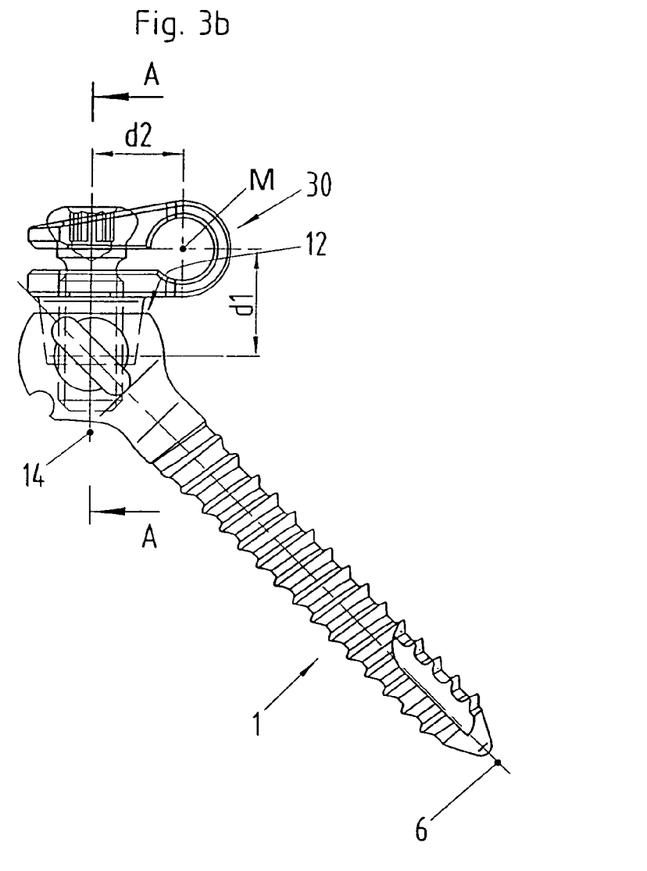
Figure 3C:
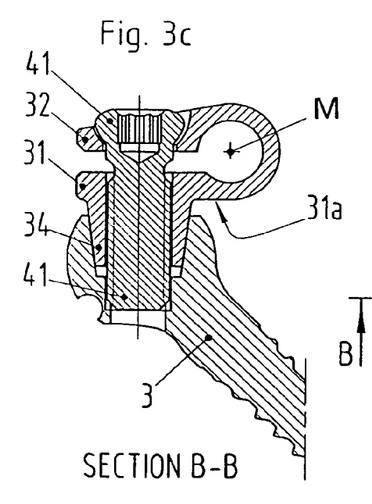
Figure 3D:
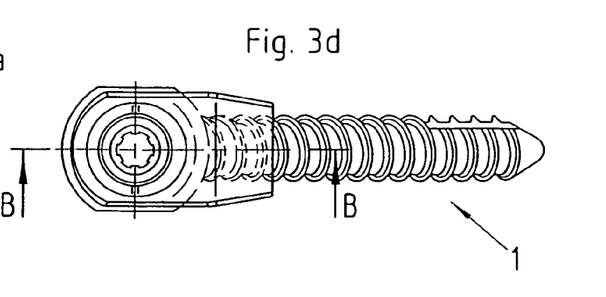

Fastening device 30, illustrated in FIG. 2, is designed in the manner of a clamp and displays one leg 31 facing towards the screw head ("lower leg") and one leg 32 facing away from it ("upper leg"), the two being connected by an arch-shaped retaining area 33, in which, for example, a longitudinal rod of a fixing device can be fixed in place. Extension 34, located on lower leg 31, can be inserted into recess 8. According to the practical example, underside 31a of lower leg 31, facing towards the screw head, is then a vertical distance away from edge 12 surrounding the recess (see FIGS. 3a, b). In this context, free face end 35 of the extension is a slight distance away from shoulder 13 surrounding threaded hole 10 on the outside, this resulting in secure, defined seating of the fastening device in recess 8. Extension 34 displays a centric through-hole 36, which transitions smoothly from the extension into lower leg 31 and is preferably of cylindrical design. Through-hole 36 is centered coaxially to threaded hole 10 by insertion of the extension into recess 8. Furthermore, leg 32, facing away from the screw head, displays a corresponding through-hole 37, the diameter of which is equal to or greater than that of the lower leg. At the same time, through-hole 36 serves as a guide, by means of which an inserted fastener, such as stud 41, can be accurately guided to the threaded section of the screw head, this greatly facilitating mounting of the fastening device. Through-hole 36 is of cylindrical design. Where appropriate, through-holes 37 and/or 36 can also expand towards the respective insertion area.

Pursuant to FIG. 3*b*, retaining area 33 of the fastening device displays a mid-point M, which is defined by the longitudinal axis of a round bar fixed in the retaining area, where, when the fastening device is mounted, the mid-point of the retaining area is located above the level of the piercing point of longitudinal axis 14 of the recess through a spherical envelope of the screw head, as illustrated schematically in FIG. 1*b*. This results in particular advantages when aligning the longitudinal rod of a spinal fixing element and when fastening it. The ratio of distance d1, which is the distance of the plane running through mid-point M and perpendicular to longitudinal axis 14 of the recess from the intersection of longitudinal axis 14 of the recess and longitudinal axis 6 of the screw shank, to distance d2 of mid-point M of the retaining area from the longitudinal axis of the recess is $\geq 1.0$ to 1.05, preferably $\geq 1.1$ to 1.25, for example approximately 1.3 or greater.

The through-hole of the extension for the stud is preferably not provided with a thread, or not with a thread that can interact with the stud. Preferably, the through-hole has a smooth wall. Preferably, the extension is dimensionally stable when the stud is passed through and/or the extension is fixed in place on the screw head.

Furthermore, with the arrangement of the fastening device on the screw head by means of an extension engaging the screw head, according to the invention, the bone screw can particularly simply be designed in such a way that it can be screwed into the associated bone up to the screw head in all possible target positions of the fastening device, where the underside of the fastening device, facing towards the shank, is always a slight distance away from the bone. The fastening device can thus be rotated virtually freely about the longitudinal axis of the recess.

The bone screw according to the invention, with an associated fastening device that engages the recess of the screw head with a retaining area, thus makes it possible that the fastening device is securely retained on the screw head, even in pre-mounted condition, that a secure hold of the fastening device is enabled even without toothing on the surface of the spherical head, and that the fastening device can absorb high forces, even if, for example, the longitudinal support of a spinal fixing element has to be deformed to align the corresponding spinal column of a patient. Furthermore, the bone screw with fastening device can be implanted by minimal invasive surgery.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

LIST OF REFERENCE NUMBERS

1 Screw
2 Thread
3 Shank
4 Screw head
5 Flat area
6 Longitudinal axis of the shank
7 Groove
8 Recess
9 Groove
10 Threaded hole
11 Insertion opening
12 Edge
13 Shoulder
14 Longitudinal axis
15 Inner wall
16 Lateral surface
16*a* Lateral surface
17 Mid-point
18 Through-hole
19 Fastening device
31 Leg
31*a* Underside
32 Leg
33 Retaining area
34 Extension
34*a* Lateral surface
35 Face end
36, 37 Through-hole
38 Plane area
39 Contact area
41 Stud
42 Groove
M Mid-point

The invention claimed is:

1. A bone screw for attaching a spinal fixing element comprising:
a screw shank that can be fixed in place in a bone, the screw shank having a thread for screwing into the bone;
a screw head; and
a fastening device including a fastener, a retaining area for mounting the spinal fixing element, and a fastening area for mounting the fastening device on the screw head;
the screw head including a fastening area for receiving the fastening device, the fastening area including a threaded section for fixing the fastening device in place;
the screw head fastening area including a recess having an opening, a stepped inner wall, a wide portion, a narrow portion, and a longitudinal axis, the wide portion being threadless and adjacent the opening, and the narrow portion being threaded and distant from the opening;
the fastening area of the fastening device including an extension for engaging the inner wall of the wide portion of the recess of the screw head, the extension being fixable in place in non-rotating fashion in the recess by means of the fastener engaging the narrow portion of the recess, and when not fixed in place, the extension being rotatable about the longitudinal axis of the recess relative to the screw head, at least over part of a circumference of the recess;
the fastening device further including a first leg facing the screw head and a second leg facing away from the screw head, between which the spinal fixing element can be fixed in place;

the extension being provided with a centered through hole extending in its longitudinal direction for receiving the fastener;

the extension being arranged at the first leg facing the screw head and protruding towards the screw head;

wherein d1 is the distance of a plane, which is running through a mid-point M of the retaining area of the fastening device and is perpendicular to a longitudinal axis of the recess, from an intersection of the longitudinal axis of the recess and a longitudinal axis of the screw shank, and wherein d2 is the distance of the mid-point M of the retaining area of the fastening device from the longitudinal axis of the recess, the fastening device being designed in that a ratio d1:d2 is $\geqq 1.0$;

wherein the fastener fastens the fastening device to the screw head fastening area and simultaneously is adapted to fasten the spinal fixing element in place on the bone screw.

2. Bone screw according to claim 1, characterized in that the recess for accommodating the extension is of essentially cylindrical design, or displays a non-circular cross-section with contact areas for retaining the extension that lie on an envelope with the shape of an arc of a circle, and in that the threaded section is located essentially concentrically to the recess.

3. Bone screw according to claim 1, characterized in that, referred to the threaded section, the recess for accommodating the extension is located facing towards the surface of the screw head and displays a larger cross-section than the threaded section.

4. Bone screw according to claim 1, characterized in that the threaded section is designed as a threaded hole, and in that the recess and the threaded hole are designed in the manner of a stepped hole.

5. Bone screw according to claim 1, characterized in that the recess tapers towards the inside of the screw head.

6. Bone screw according to claim 1, characterized in that a shoulder radially surrounding the threaded section on the outside displays a larger radial extension than an edge radially surrounding the recess on the outside.

7. Bone screw according to claim 1, characterized in that, on a side of the recess most closely adjacent to the screw shank, a height of an inner wall of the recess extends beyond an extension of a lateral surface of the screw shank into the screw head.

8. Bone screw according to claim 1, characterized in that a cross-sectional area bounding a depth of the threadless recess is located roughly at the level of, or on, the side of an intersection of a longitudinal axis of the screw and the longitudinal axis of the recess facing away from the opening of the recess.

9. Bone screw according to claim 1, characterized in that the screw head is essentially designed as a spherical head or a partially spherical head.

10. Bone screw according to claim 1, characterized in that the recess is designed as a through-hole passing through the screw head.

11. Bone screw according to claim 1, characterized in that the extension of the fastening device is of essentially cylindrical design and displays a through-hole for a connecting element for fixing the fastening device in place on the screw head.

12. Bone screw according to claim 1, characterized in that, in a fastened position of the fastening device, the first leg faces towards the screw head and the second leg faces away from the screw head, between which the spinal fixing element can be fixed in place; and wherein the extension of the fastening device is located on the first leg that faces towards the screw head.

13. Bone screw according to claim 1, characterized in that the extension tapers towards its free end.

14. Bone screw according to claim 1, characterized in that, when the fastening device is fixed in place, only partial areas of a lateral surface of the extension located in the recess are in contact with an inner wall of the recess.

15. Bone screw according to claim 1, characterized in that the mid-point M of the retaining area for fixing the spinal fixing element in place is located roughly at the level of, or above, a plane of the screw head that includes a piercing point of the longitudinal axis of the recess through a surface of a sphere of the screw head and is located perpendicular to the longitudinal axis of the recess.

16. Bone screw according to claim 1, characterized in that the fastening device is provided with a guide for the fastener for fixing the fastening device in place on the screw head, the fastener being accurately guidable to the threaded section of the screw head by means of the guide.

17. Bone screw according to claim 1, characterized in that, when the fastening device is fixed in place, an end of the extension of the fastening device facing away from the retaining area for the spinal fixing element is a distance away from an end of the threadless recess, and an end of the extension of the fastening device facing towards the retaining area for the spinal fixing element projects from the threadless recess.

* * * * *